United States Patent [19]

Sujeeth

[11] Patent Number: 5,468,862
[45] Date of Patent: Nov. 21, 1995

[54] SYNTHESIS OF SOLVENT YELLOW 33 (D & C YELLOW 11) WITH EXCESS PHTHALIC ANHYDRIDE ACID AS A SOLVENT

[75] Inventor: Puthalath K. Sujeeth, Maryland Heights, Mo.

[73] Assignee: Warner-Jenkinson Company, St. Louis, Mo.

[21] Appl. No.: 232,703

[22] Filed: Apr. 25, 1994

[51] Int. Cl.$^6$ ................................ C07D 215/14
[52] U.S. Cl. ................................ 546/173
[58] Field of Search ............................ 546/173

[56] References Cited

U.S. PATENT DOCUMENTS

| | | | |
|---|---|---|---|
| 1,963,374 | 6/1934 | Ogilvie | 546/173 |
| 2,592,370 | 4/1952 | Zwilgmeyer | 546/154 |
| 3,036,876 | 5/1962 | Schoellig et al. | 8/512 |
| 3,108,109 | 10/1963 | Clarke | 546/101 |
| 3,301,676 | 1/1967 | Tomanek | 430/124 |
| 3,767,357 | 10/1973 | Spietschka et al. | 8/638 |
| 3,872,131 | 3/1975 | Wallace | 546/154 |
| 3,932,419 | 1/1976 | Groll | 546/154 |
| 3,972,885 | 8/1976 | Kimura | 546/154 |
| 4,088,651 | 5/1978 | Kalz | 546/154 |
| 4,150,025 | 4/1979 | Shimada | 546/99 |
| 4,373,102 | 2/1983 | Neumann et al. | 544/143 |
| 4,398,916 | 8/1983 | Ambrosiano et al. | 8/602 |
| 4,656,268 | 4/1987 | Adam | 544/126 |
| 5,106,980 | 4/1992 | Ort et al. | 546/167 |

FOREIGN PATENT DOCUMENTS 1362 of 1883 United Kingdom.

OTHER PUBLICATIONS

Manly, et al,. "A Study of the Chemistry of Pyrophthalone and Related Compounds", *Pyrophthalone and Related Compounds*, vol. 23, pp. 373–380 (Mar., 1958).

Eibner, et al., "Zur Constitution des Chinophtalons und der beiden isomeren Chinophtaline", Am. 315, 303–356 (1901).

*Primary Examiner*—C. Warren Ivy
*Assistant Examiner*—D. Margaret M. Mach
*Attorney, Agent, or Firm*—Whyte Hirschboeck Dudek

[57] ABSTRACT

A process for the manufacture of a quinophthalone, in particular Solvent Yellow 33 (D & C Yellow 11) is described. The quinophthalone, in particular Solvent Yellow 33, is made by a process in which quinaldine is condensed with a molar excess of either phthalic acid or phthalic anhydride, the acid or anhydride being employed not only as a reactant, but also as a solvent for the reaction. This process can also employ phthalic acid (or recycled phthalic acid) and phthalic anhydride together, one as the solvent and the other as the reactant.

7 Claims, No Drawings

SYNTHESIS OF SOLVENT YELLOW 33 (D & C YELLOW 11) WITH EXCESS PHTHALIC ANHYDRIDE ACID AS A SOLVENT

BACKGROUND OF THE INVENTION

1. Field of the Invention

This invention relates to a process for the manufacture of quinophthalone dyes, in particular Solvent Yellow 33, also known as D & C Yellow 11. In one aspect, the invention relates to the manufacture of Solvent Yellow 33 by condensation of quinaldine with excess phthalic anhydride which is employed both as a solvent and as a reactant. In another aspect, the invention relates to the manufacture of Solvent Yellow 33 by condensation of quinaldine with excess phthalic acid in which the acid is used both as a solvent and as a reactant. In yet another aspect, the invention relates to the use of both phthalic anhydride and phthalic acid, one as a reactant and the other as a solvent for the reaction. In still another aspect, the invention relates to the use of recycled phthalic acid as a solvent for the reaction.

2. Description of the Prior Art

The classical method for manufacturing dyes is described in British Patent No. 1362 issued to Denton. Denton teaches a process which involves the condensation of pyridine or chinoline bases with phthalic anhydride in the presence of zinc chloride.

Improvements to this method have occurred since Denton. Today, the conventional process for the manufacture of quinoline yellow dyes is to react a quinaldine derivative with phthalic anhydride in the presence of an inert organic liquid employed as either a solvent or as a diluent (see U.S. Pat. No. 1,963,374 to Ogilvie). For example, Ort, et al. teaches in U.S. Pat. No. 5,106,980 a process for the preparation of a quinophthalone by condensing 8-aminoquinaldine with a phthalic anhydride in the presence of molten benzoic acid acting as diluent and promoter.

Other prior art references disclose methods of manufacturing quinoline yellow dyes, such as 2-(2-quinoyl-6-sulfonic acid)-1,3-indandione (also known as D & C Yellow 10) and 2-(2-quinoyl-6-sulfonic acid)-1,3-indandione-5-sulfonic acid (also known as E 104). These water soluble dyes can be manufactured either by a two-step process which involves a condensation reaction and then the sulfonation of the quinophthalone or a one step process which involves the condensation of a sulfonated intermediate. Clarke, for example, teaches the one step process in U.S. Pat. No. 3,108,109. Specifically, he teaches that quinaldine sulfonic acid can be condensed with phthalic anhydride in the presence of a reaction promoter selected from the group consisting of dimethylacetamide, dimethylformamide and mixtures of the said amide reaction promoters. Sulfonated intermediates, however, cannot be used in the direct manufacture of Solvent Yellow 33.

SUMMARY OF THE INVENTION

According to this invention, a quinophthalone, in particular Solvent Yellow 33, is made by a process in which a quinaldine is condensed with a molar excess of either a phthalic anhydride or a phthalic acid, the phthalic anhydride or acid being employed not only as a reactant, but also as a solvent for the reaction. In one embodiment, the acid and anhydride are used together, one as the reactant and the other as the solvent. In another embodiment, recycled phthalic acid is used as the solvent for the reaction. As used herein, "phthalic acid" includes both phthalic acid per se and substituted phthalic acid, both of any grade. Substituted phthalic acid refers to a phthalic acid bearing one or more substitutents, preferably inert substitutents. Inert substitutents are those that are for all intent and purposes essentially nonreactive with the starting materials and products of the process at process conditions (e.g. alkyl, halogen etc.).

As used herein, "recycled phthalic acid" refers to phthalic acid per se and substituted phthalic acid which is a by-product of the condensation reaction between quinaldine and phthalic anhydride which is recovered, recycled and used as the solvent in subsequent condensation reactions. Substituted phthalic acid refers to a phthalic acid bearing one or more substitutents, preferably inert substitutents. Inert substitutents are those that are for all intent and purposes essentially nonreactive with the starting materials and products of the process at process conditions (e.g. alkyl, halogen etc.).

As used herein, "quinaldine" includes both quinaldine per se and substituted quinaldine, both of any grade. Further, as used herein, "phthalic anhydride" includes both phthalic anhydride per se and substituted phthalic anhydride, both of any grade. Substituted quinaldine and substituted phthalic anhydride refer to a quinaldine and phthalic anhydride, respectively, bearing one or more substitutents, preferably inert substitutents. Inert substitutents are those that are for all intent and purposes essentially nonreactive with the starting materials and products of the process at process conditions (e.g. alkyl, halogen etc.).

The quinophthalones of this invention include a broad class of known compounds which have been generally described in the following references: British Patent No. 1362 issued to Denton, Straley, J. M., "Disperse Dyes", *The Chemistry of Synthetic Dyes,* Vol. III, edited by K. Venkataraman, pages 454–457 (1970), Manly, et al., "A Study of the Chemistry of Pyrophthalone and Related Compounds," J.O.C., 23, 373–380 (1958), and Eibner and Lange, "The Constitution of Chinophthalones and Two Isomeric Chinophthaleins," Ann 315, 303–356 (1901), all of which are incorporated herein by reference. The quinophthalone of formula I, known as Solvent Yellow 33 (also known as D & C Yellow 11), is the preferred quinophthalone of this invention.

This invention offers several advantages over other known methods of manufacturing quinophthalones, in particular Solvent Yellow 33. First, by employing a phthalic anhydride and/or its hydrated equivalent, a phthalic acid, as both a reactant and a solvent, the process eliminates the opportunity for contamination of the final product by impurities, such as benzoic acid, which later require removal. Second, disposal of unreacted reactants or resulting by-products is unnecessary because they are recycled for use in subsequent reactions to make additional end-product.

DETAILED DESCRIPTION OF THE INVENTION

Quinophthalones, and in particular Solvent Yellow 33 of formula I

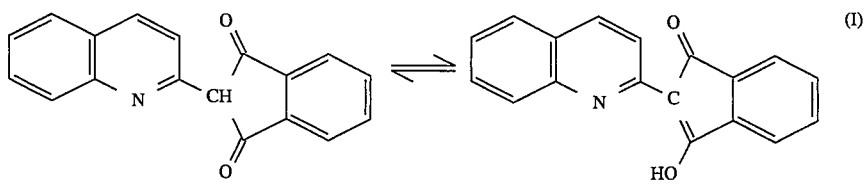

which exists in tautomeric equilibrium, can be prepared by condensing quinaldine of formula II

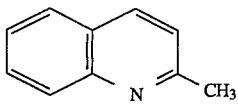

with excess phthalic anhydride of formula III

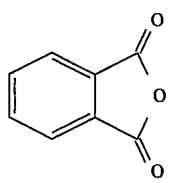

or excess phthalic acid of formula IV

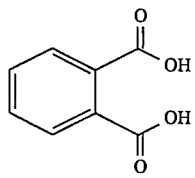

the phthalic anhydride or phthalic acid employed as both a reactant and a solvent for the reaction.

Quinophthalones, in particular Solvent Yellow 33, can also be prepared by condensing quinaldine and phthalic anhydride in the presence of phthalic acid or recycled phthalic acid, the latter present as a solvent.

Phthalic acid is the hydrated equivalent of phthalic anhydride, and it can be employed as the solvent for the reaction between quinaldine and phthalic anhydride. Any grade, e.g. technical grade, of phthalic acid may be used.

Recycled phthalic acid is also a reactant and solvent for the process of this invention. Recycled phthalic acid is the result of base neutralization and subsequent acidification of excess phthalic anhydride at the end of the quinaldine/phthalic anhydride condensation. Typically at the end of this condensation reaction, any suitable base is used with the reaction mass to convert the excess phthalic anhydride to the corresponding salt. This salt is then precipitated by acidification from the neutralized reaction mass, i.e. the original mother liquor, by addition of any suitable acid, e.g. 50% sulfuric acid ($H_2SO_4$), and then isolated. Typically, about 80% of the original phthalic anhydride can be recovered as phthalic acid.

Because these dyes have drug and cosmetic applications, FDA approval is required. FDA approval is dependent on, among other things, product purity which for practical purposes is best controlled through batchwise purification. The process, however, may be adapted so as to be carried out continuously. Preferably, the process is operated at atmospheric pressure or at a slightly reduced pressure. One of the advantages of this process is that it does not require dedicated equipment and thus on an industrial scale, the process can be conducted in multi-purpose equipment such as conventional closed reactors capable of operation at high temperatures.

The reaction temperature of this process is not critical to the invention, and can vary to convenience and will depend on, among other things, the reactants and equipment. Typically, the reaction mixture or mass is heated to a temperature of at least about 175 C., preferably at least about 185 C. The maximum temperature, however, generally does not exceed 225 C., preferably it does not exceed 215 C.

In the condensation reaction involving quinaldine and phthalic anhydride, the phthalic anhydride is used in a stoichiometric excess relative to quinaldine. The maximum excess is a factor based on economy and convenience. Typically, however, the maximum excess does not exceed 5, preferably it does not exceed 3.

In the condensation reaction involving quinaldine and phthalic acid and/or recycled phthalic acid, the phthalic acid and/or recycled phthalic acid is similarly used in a stoichiometric excess relative to quinaldine. The maximum excess is a factor based on economy and convenience. Typically, however, the maximum excess does not exceed 5, preferably it does not exceed 3.

In the condensation reaction involving quinaldine, phthalic anhydride and phthalic acid and/or recycled phthalic acid, the phthalic anhydride and the phthalic acid and/or recycled phthalic acid are also used in a stoichiometric excess relative to quinaldine. The maximum excess is a factor based on economy and convenience. Typically, however, the maximum excess does not exceed 5, preferably it does not exceed 3. The phthalic acid and/or the recycled phthalic acid, which is used as a solvent for the reaction, is used in an amount which is usually from greater than 0 to about 2 moles, preferably from about 0.8 to about 1.2 moles, for each mole of quinaldine.

If water is associated with any of the reactants, the time required to complete the condensation of quinaldine and phthalic anhydride is generally longer than if the reactants were anhydrous. Depending upon the amount of water in the reactants, the time required to complete the condensation varies from about 2 to 10 hours. For example, a reaction which uses dry reactants generally requires about 2 hours for completion. Recycled phthalic acid, however, typically contains from about 20% to 70% water and as such, can require from about 2 to 8 hours to remove the water from the reaction mixture.

Although not required upon completion of the condensation, the temperature of the reaction mixture is typically lowered by about 25 C. before the reaction mixture is quenched into water to form a slurry. A basic reagent, such as an alkali or an ammonium hydroxide, is added to the slurry to react with the excess phthalic acid or phthalic anhydride to form the corresponding salt. Any grade of base solution can be used; however, 50% caustic soda solution is usually used. The amount of base reagent added is a function of the length of time necessary to complete the hydrolysis. Typically, a sufficient amount of base reagent is added to raise the pH of the slurry to between about 7 and 11.5. Generally, the more basic (e.g. the larger the pH number), the faster the hydrolysis. Hydrolysis can occur at a pH in excess of 11.5, but generally results in an orange color as opposed to the desired yellow, due to the ionization of the products. The slurry is then heated to a temperature of between about 45 C. to about 75 C., preferably about 55 C. to 60 C. for 2 to 4 hours. The quinophthalone, in particular Solvent Yellow 33 of formula I, can be isolated by filtration and washed with dilute acid and hot water.

The process of this invention typically produces yields of quinophthalones, in particular Solvent Yellow 33, in excess of 85% and is essentially free of contaminants. Furthermore, our process reduces product waste by recovering and recycling the unreacted reactants or resulting by-products. The process also avoids the chance of contamination of the final product by solvent impurities which would later require removal.

The invention is further described by the following Examples. Unless otherwise indicated, all parts and percentages are by weight.

SPECIFIC EMBODIMENT

Example 1

Quinaldine (82.4 g of 86% strength) was added to a one liter jacketed glass vessel followed by phthalic anhydride flakes (200 g). The mixture was heated to 200 C. and held at 200–215 C. for approximately 2 hours while the water was removed by distillation. Upon completion, the reaction mixture was then transferred to a stirred vessel containing water (750 g). The quench mixture, a yellow brown slurry, was heated from 45 C. to 60 C. and mixed for one half hour. To this quench mixture, a sodium hydroxide solution (126.9 g of 50% strength) was added to a final pH of 10.7. The resulting slurry was filtered in vacuo, rinsed with hot water (484 g) and then washed with sulfuric acid (50 g of 50% strength diluted with 500 g water). The filter cake was washed to neutrality with water (780 g) and a yellow cake (255.5 g) was obtained. This upon drying and grinding yielded Solvent Yellow 33 (134 g) of the formula I.

50% Sulfuric acid (149.4 g) was added to the original filtration mother liquor and cooled to ambient temperature in order to precipitate the phthalic acid (182 g). The phthalic acid is recovered and recycled for use in the preparation of Solvent Yellow 33.

The Solvent Yellow 33 and the quinaldine in the product stream was analyzed using the following HPLC method:

TABLE I-A

| HPLC Method | | | | |
|---|---|---|---|---|
| COLUMN | HYPERSIL C8, 25 cm × 4.6 mm | | | |
| MOBILE PHASE | A-0.1 M AMMONIUM ACETATE IN WATER B-METHANOL | | | |
| INJECTION VOLUME | 20 MICROLITERS | | | |
| COLUMN TEMPERATURE | AMBIENT | | | |
| DETECTOR | 254 nm @ 0.1 AUFS | | | |
| FLOW RATE | 1.0 ml/min | | | |
| GRADIENT PROGRAM | TIME | % A | % B | CURVE |
| | 0 | 100 | 0 | * |
| | 25 | 0 | 100 | LINEAR |
| TYPICAL | PHTHALIC ANHYDRIDE | | | 3.2 MIN |

TABLE I-A-continued

| HPLC Method | | |
|---|---|---|
| RETENTION TIMES | QUINALDINE | 22.2 MIN |
| | D & C YELLOW #11 | 27.1 MIN |

The phthalic acid in the precipitate was analyzed using the following method:

Methanol (20 ml) was added to the sample (0.10 g to 0.15 g) and mixed to dissolve. Water (80 ml) was then added to this mixture. Sodium hydroxide solution (0.1 N) was used to titrate the mixture to a potentiometric endpoint (at about −60 mv). One ml of 0.1N NaOH is equivalent to 8.306 mg phthalic acid.

The composition of the product stream (from the above experiments), as determined by the HPLC method and the Phthalic Acid analysis described above, is reported in TABLE I-B.

TABLE I-B

| Composition of the Product Stream | | | | | |
|---|---|---|---|---|---|
| | Powder | Distillate | Wash | Precipitate | Mother Liquor |
| Solvent Yellow (33%) | 93.0 | NA | <0.01 | NA | NA |
| Phthalic acid (%) | <0.1 | <0.1 | 0.37 | 99.7 | 0.81 |
| Quinaldine (%) | <0.1 | 0.89 | 0.12 | 0.10 | 0.01 |

NA = Not Analyzed

Example 2

Wet recovered phthalic acid (112 g) was placed in a one-liter jacketed glass vessel. Quinaldine (83.2 g of 86% strength) was added to the vessel followed by phthalic anhydride flakes (100 g). The mixture was heated to 200 C. and held at 200–215 C. for approximately 2 hours while the water was removed by distillation. Upon completion, the reaction mixture was then cooled to 190 C., and was then transferred under nitrogen pressure to a stirred vessel containing water (760 g). The quench mixture, a yellow brown slurry, was heated from 45 C. to 60 C. and mixed for one half hour. To this quench mixture, 50% sodium hydroxide solution (112.5 g) was added to a final pH of 11.5 and mixed overnight. The resulting slurry was filtered in vacuo, rinsed with hot water (1313 g) and then washed with 4.5% sulfuric acid (550 g). The filter cake was washed to neutrality with water and a yellow cake (265.8 g) was obtained. This upon drying and grinding yielded Solvent Yellow 33 (131.4 g) of the formula I.

50% Sulfuric acid (130 g) was added to the original filtration mother liquor and cooled to ambient temperature in order to precipitate the phthalic acid (97.7 g). The phthalic acid is again recycled and can be used in the preparation of Solvent Yellow 33.

The composition of the product stream from the above experiment, as determined by the HPLC method and the phthalic acid analysis as described in Example 1, is reported in Table II.

TABLE II

| | Composition of the Product Stream | | | |
|---|---|---|---|---|
| | Powder | Wash | Precipitate | Mother Liquor |
| Solvent Yellow (33%) | 89.7 | NA | <0.01 | NA |
| Phthalic acid (%) | <0.1 | 1.08 | 90.8 | 0.56 |
| Quinaldine (%) | <0.1 | 0.29 | 0.14 | 0.01 |

NA = Not Analyzed

Example 3

Quinaldine (77 g of 86% strength) and phthalic acid powder (206.5 g) were added to a 500-ml Fisher reaction kettle fitted with a thermometer, Dean-Stark trap with condenser and a mechanical stirrer. The mixture was heated to 212 C. and held at 191–212 C. for approximately 2 hours while the water was removed by distillation. Upon completion, the reaction mixture was transferred to a stirred vessel containing water (841 g). The quench mixture, a yellow brown slurry, was heated from 45 C. to 60 C. and mixed for one half hour. To this quench mixture, a sodium hydroxide solution (128.7 g of 50% strength) was added to a final pH of 11.5 and mixed overnight. The resulting slurry was filtered under vacuum, rinsed with hot water (25 ml) and then washed with 5.0% sulfuric acid (280 g). The filter cake was washed to neutrality with water (1 l) and a yellow cake (275.9 g) was obtained. This upon drying and grinding yielded Solvent Yellow 33 (126.2 g) of the formula I.

50% Sulfuric acid (173.1 g) was added to the original filtration mother liquor (1325 g) and cooled to ambient temperature in order to precipitate the phthalic acid (117.3 g). The phthalic acid is recovered and recycled for use in the preparation of Solvent Yellow 33.

The composition of the product stream from the above experiment, as determined by the HPLC method and the phthalic acid analysis as described in Example 1, is reported in Table III.

TABLE III

| | Composition of the Product Stream | | | |
|---|---|---|---|---|
| | Powder | Distillate | Wash | Precipitate |
| Solvent Yellow (33%) | 95.1 | <0.01 | NA | NA |
| Phthalic acid (%) | <0.1 | 3.94 | 0.43 | 92.9 |
| Quinaldine (%) | <0.1 | 0.96 | 0.14 | <0.1 |

NA = Not Analyzed

The foregoing description and examples are for the purpose of illustration only, and does not limit the scope of protection which should be accorded this invention.

What is claimed is:

1. A process for the preparation of a quinophthalone comprising the steps of:

(A) condensing a neat reaction mixture of quinaldine and a stoichiometric excess amount of a reagent, wherein the reagent is selected from the group consisting of phthalic anhydride, phthalic acid and mixtures thereof;

(B) quenching the reaction mixture with water;

(C) adding a base to the reaction mixture in an amount sufficient to react with the excess amount of reagent to form a phthalic acid salt;

(D) isolating the quinophthalone from the reaction mixture.

2. The process of claim 1, further comprising the step of:

(E) recycling the reaction mixture obtained from step (D) for use as the reagent in the condensation reaction of step (A).

3. The process of claim 1 wherein the quinophthalone has the formula:

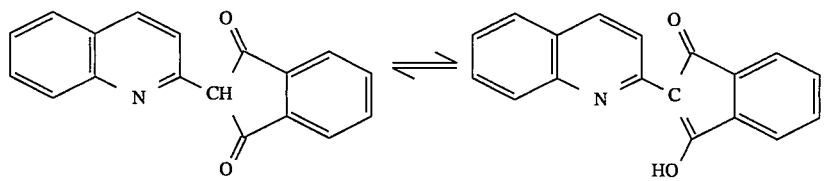

the quinaldine has the formula:

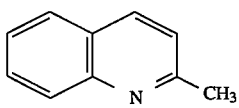

the phthalic anhydride has the formula:

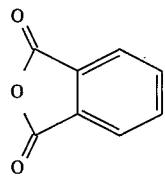

and phthalic acid has the formula:

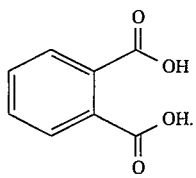

4. A process for the preparation of a quinophthalone of the formula:

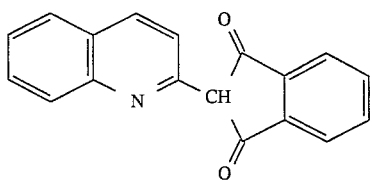 ⇌ 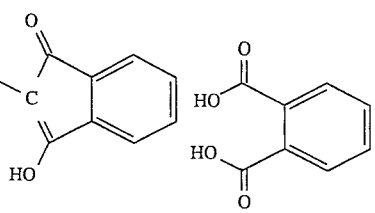

and phthalic acid of the formula:

comprising the steps of:

(A) condensing a neat reaction mixture of quinaldine of the formula:

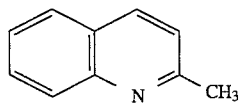

and up to about 5 moles of a reagent per mole of quinaldine at a temperature from about 175 C. to about 225 C., wherein the reagent is selected from the group consisting of phthalic anhydride of the formula:

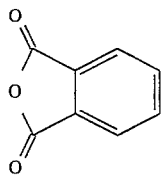

and mixtures thereof;

(B) quenching the reaction mixture with water;
(C) adding a base to the reaction mixture in an amount sufficient to react with the excess amount of reagent to form a phthalic acid salt;
(D) isolating the quinophthalone from the reaction mixture.

5. The process of claim 4, further comprising the step of:
(E) recycling the reaction mixture obtained from step (D) for use as the reagent in the condensation reaction of step (A).

6. The process of claim 1 wherein the reaction mixture is condensed at a temperature from between about 175 C. to about 225 C.

7. The process of claim 1 wherein up to about 5 moles of the reagent is used per mole of quinaldine.

* * * * *